United States Patent [19]
Jeffers et al.

[11] Patent Number: 5,486,915
[45] Date of Patent: Jan. 23, 1996

[54] ON-LINE MEASUREMENT OF LIGNIN IN WOOD PULP BY COLOR SHIFT OF FLUORESCENCE

[75] Inventors: Larry A. Jeffers, Washington Township, Stark County; Michael L. Malito, Liberty Township, Trumbull County, both of Ohio

[73] Assignee: The Babcock & Wilcox Company, New Orleans, La.

[21] Appl. No.: 226,801

[22] Filed: Apr. 12, 1994

[51] Int. Cl.$^6$ .............................. G01N 21/64; D21C 7/14
[52] U.S. Cl. .......................... 356/318; 250/461.1; 162/49
[58] Field of Search ...................................... 356/317–318, 356/417; 250/458.1, 459.1, 461.1, 462.2; 162/49, 198, 263

[56] References Cited

U.S. PATENT DOCUMENTS

| | | | |
|---|---|---|---|
| 5,166,755 | 11/1992 | Gat | 356/419 |
| 5,216,483 | 6/1993 | Berthold et al. | 356/318 |
| 5,220,172 | 6/1993 | Berthold et al. | 250/461.1 |

OTHER PUBLICATIONS

Tappi Test Methods, 1991, vol. 1, T236–CM 85, "Kappa Number of Pulp".
Klemhart, T. N. E Joyce, C. S. "Short Wavelength Ultraviolet Absorption of Various Lignin & Related Substances, Part I," Pulp & Paper Mag of Canada, Apr. 1957, pp. 131–148.
Joyce, C. S. & Kleinhart, T. N, "Short Wavelength Ultraviolet Absorption of Various Lignins & Related Substances", Part II Pulp & Paper Mag of Canada, May 1957, pp. 131–148.
Kleinhart T. N. & Joyce S. "Short Wavelength Absorption of Various Lignins & Related Substances", III, Pulp & Paper Mag Canada, Jun. 1957, pp. 215–219.
Kleinhart, T. N. & Joyce C. S. "Short Wavelength Absorption of Various Lignins & Related Substances IV", Pulp & Paper Mag of Canada, Oct. 1957, pp. 147–152.
Hartler, N. Norrstrom H., "Light Absorbing Properties of Pulp & Pulp Components III" TAPPI Journal, vol. 52, No. 9, Sep. 1969.
Norrstrom, B. & Teder, A., "Absorption Bands in Electronic Spectra of Lignins" Svensk Papperstidning, 15 Jun. 1971, pp. 337–344.
Sjöstrom, E., Haglund, P., "Spectrophotometric Determination of the Dissolution of Lignin During Sulfite Cooking" TAPPI, vol. 47, No. 5, May, 1964 pp. 286–291.
Bublitz, W, "Fluorescence of Pulping Liquors: A Tool for Diaster Control?", TAPPI vol. 64, Jun. 1981, pp. 73–76.
Baumgartner, D. J., Fledman, M. H., Gibbons, C. L. "A Procedure for Tracing Kraft Mill Effluent from an Ocean by Constituent Fluorescence" Water Research, Pergamon Press, vol. 4, 1971, pp. 533–544.
Bublitz, W. J. & Wade, D. C., "Applied Waste Liquor Fluorescence to Control Pulp Quality", Svensk Papperstidning, No. 18, 1979, pp. 535–538.
Wilander, A., Kvarnes, H. & Lindell, T. "A Modified Fluorometric Method for Measurement of Lignin Sulfonates & Its in–situ Application in Natural Waters", Water Research, vol. 8, 1974, pp. 1037–1045.
Demas, J. N. "Excited State Lifetime Measurements", Academic Press, NY, 1983 pp. 53–58.
Tikka, P. O. & Virkoka, N. E., "A New Kraft Pulping Analyzer for Monitoring Organic & Inorganic Substances," TAPPI Journal Jun. 1966, pp. 66–71.
Williams, D. J., "The Application of the Ultra Violet Absorp (List continued on next page.)

Primary Examiner—Vincent P. McGraw
Assistant Examiner—K. P. Hantis
Attorney, Agent, or Firm—Robert J. Edwards; Eric Marich

[57] ABSTRACT

Lignin concentrations from wood pulp samples are measured by applying an excitation light at a selected wavelength to the samples in order to cause the lignin to emit fluorescence. A spectral distribution of the fluorescence emission is then determined. The lignin concentration is then calculated based on the spectral distribution signal. The spectral distribution is quantified by either a wavelength centroid method or a band ratio method.

23 Claims, 6 Drawing Sheets

OTHER PUBLICATIONS tion Characteristic of Lignin to the Control of Pulp Uniformity" Appita vol. 22, No. 2, Sep. 1968, pp. 45–52.

Capart R. Obese–Jeery, K, LeCardinal G., Gelus, M. "Contribution to On–Line Kraft Pulping Control", PRP 4 Proceedings Chent 1980, pp. 121–128.

BTG Sales "Kappa Number Analyzer", B 218.66 e–a Entire Paper–Product Brochure, Date Unknown.

Product Brochure–Asea Brown Boveri–Date Unknown.

Kubulneiks, E. Sandstrom, P. "Control of Oxygen Delignification Based on On–Line Kappa Number Measurement" 1988 International Pulp Bleaching Conference pp. 47–51.

BTG–Product Brochure "KNA–500 Kappa Number Analyzer" Entire Paper–Date Unknown.

Horvath, J. J. & Semerjian, H. G. "Laser Excited Fluorescence Studies of Black Liquor" Proceedings of the SPIE, vol. 665, Jun., 1986, pp. 258–264.

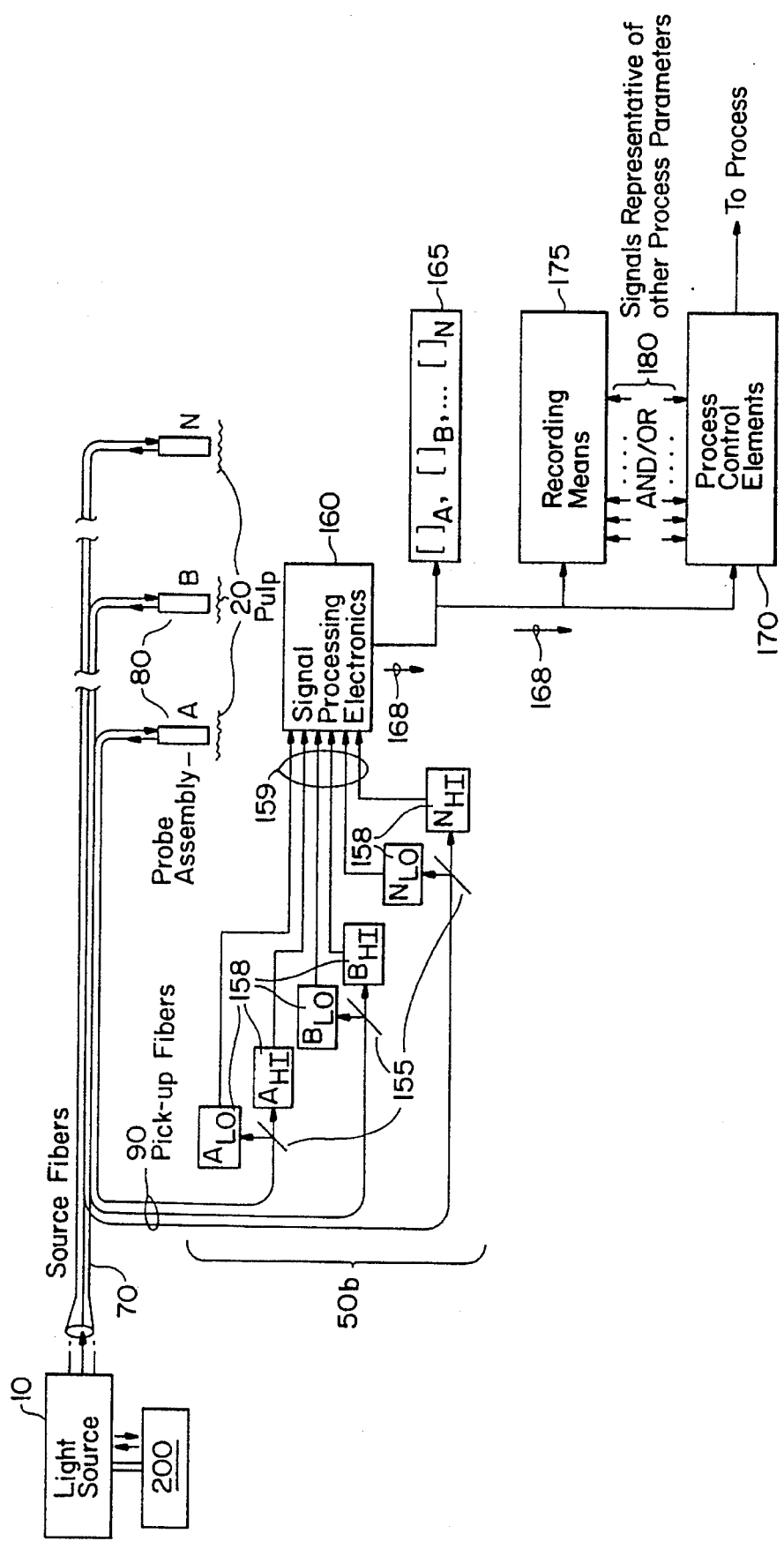

ON-LINE MEASUREMENT OF LIGNIN IN WOOD PULP BY COLOR SHIFT OF FLUORESCENCE

The Government of the United States of America has certain rights in the invention pursuant to Contract DE-FC05-09CE-40905, awarded by the U.S. Department of Energy.

FIELD AND BACKGROUND OF THE INVENTION

The present invention relates, in general, to the pulp and paper industry, and in particular, to a new and useful apparatus, system and method for on-line, in-situ monitoring and/or controlling the concentration of lignin in wood pulp and black liquor.

In the pulp and paper industry, the production of paper products requires that lignin be partially removed from the wood chip feed stock prior to making paper products. Lignin is a polymer of complex chemical structure which "cements" the wood's cellulose fibers together. The process by which lignin is removed is referred to as delignification. The most prevalent method of delignification is by chemical means in which raw wood chips and chemicals are combined at controlled pressure and temperature in a vessel known as a digester. While in the digester, the amount of lignin removed from the wood chips determines the product quality, the product yield, the amount of energy consumed, the quantity of chemicals consumed, and the product cost. Fluid drained from the digester during delignification contains lignin removed from the wood chips and is referred to as "black liquor". The black liquor is used as fuel to the boiler to produce process steam.

The measurement of the residual lignin remaining in the pulp, which exits the digester, is most commonly carried out by laboratory analysis of hourly samples of the digester output (samples are typically obtained at the last stage of the brownstock washer). The lab analysis takes approximately one hour and therefore is a poor method for providing process control feedback and cannot be used for feedforward control. This lab analysis is a back titration method which measures the consumption of potassium permanganate and is only an approximation to the lignin concentration. The output of the titration analysis is referred to as a "KAPPA Number" and the procedure is documented in TAPPI procedure T236 cm-85, "KAPPA Number of Pulp". A number of manufacturers have produced automatic sampling and titration devices which have been tried in pulp mill situations but they have been mostly unsuccessful in providing accurate long-term results and did not eliminate the hour delay between the process and measurement of residual lignin.

The ultraviolet absorption and fluorescence properties of lignin have long been known and a number of researchers have reported results of measurements in solutions containing lignin. Both the absorption techniques (e.g. see Kleinert, T. N. and Joyce, C. S., "Short Wavelength Ultraviolet Absorption of Various Lignins and Related Substances," Part I, *Pulp and Paper Magazine Can.* 58, No. 5, April 1957, pp. 154–158.; Joyce, C. S. and Kleinert, T. N., Ibid., Part II, *Pulp and Paper Magazine Can.* 58, No. 6, May 1957, pp. 131–148.; Kleinert T. N. and Joyce, C. S., Ibid., Part III, *Pulp and Paper Magazine Can.* 58, No. 7, June 1957, pp. 215–219; Kleinert T. N. and Joyce, C. S., Ibid., Part IV, *Pulp and Paper Magazine Can.* 58, October 1957, pp 147–152; Hartler, N. and Norrstrom, H., "Light Absorbing Properties of Pulp and Pulp Components," *TAPPI Journal*, Vol. 52, No. 9, September 1969; Norrstrom, B. and Teder, A., "Absorption Bands in Electronic Spectra of Lignins, Part 2, Band Intensities for Alkali Lignins from Spruce," *Svensk Papperstidning*, 15 Jun. 1971; and Sjostrom, E. and Haglund, P., "Spectrophotometric Determination of the Dissolution of Lignin During Sulfite Cooling," TAPPI Journal, Vol. 47, No. 5, May 1964, pp 286–291) and the fluorescence techniques (e.g. see Bublitz, W. J., "Fluorescence of Pulping Liquors: A Tool for Digester Control?", pp 73–76; Baumgartner, D. J., Feldman, M. H., and Gibbons, C. L., "A Procedure for Tracing Kraft Mill Effluent From an Ocean by Constituent Fluorescence," *Water Research*, Pergamom Press, Vol. 4, 1971, pp 533–544; Bublitz, W. J. and Wade, D. C., "Applied Waste Liquor Fluorescence to Control Pulp Quality," *Svensk Paploerstidnin*, No. 18, 1979, pp 535–538; Wilander, A., Kvarnas, H. and Lindell, T., "A Modified Fluorometric Method for Measurement of Lignin Sulfonates and Its In-Situ Application in Natural Waters," Water Research, Vol. 8, 1974, pp 1037–1045; and Demas, J. N., *Excited State Lifetime Measurements*, Academic Press, New York, 1983, pp 53–58), have all been applied to very dilute solutions.

The fluorescence techniques have been used primarily as a method of detecting trace quantities in effluent streams. All of these approaches made use of very dilute lignin solutions where the absorption and fluorescence signal are linearly related to lignin concentration. The concentration of lignin in these solutions is typically 2000–10,000 times more dilute than the concentration of lignin in "black liquor" found in the pulping process. Thus, use of these techniques requires precise sample preparation prior to measurement. A number of devices which attempt to monitor the lignin concentration in "black liquor" during the pulping process by UV absorption techniques (alone or in combination with chemical analysis) have been produced. See Tikka, P. O., and Virkoka, N. E., "A New Kraft Pulping Analyzer for Monitoring Organic and Inorganic Substances," *TAPPI Journal*, June 1966, pp 66–71; Williams, D. J., "The Application of Ultra-Violet Absorption Characteristic of Lignin to the Control of Pulp Uniformity," *Appita*, Vol. 22, No. 2, September 1968, pp 45–52; and Capart, R., Obese-Jecty, K., Le Cardinal, G., and Gelus, M., "Contribution to the On-Line Kraft Pulping Control," *PRP 4 Proceedings*, Ghent, 1980, pp 121–128. These devices require sample preparation and dilution prior to measurement and are therefore not in-situ, not real-time, and introduce sampling and dilution errors.

Use of ultraviolet absorption has recently been extended to the measurement of residual lignin in wood pulp (see Kubulnieks, E., Lundqvist, S., and Pettersson, T., "The STFI OPTI-Kappa Analyzer, Applications and Accuracy," *TAPPI Journal*, November 1987, pp 38–42). This device is marketed by Asea Brown Boveri under the trade name "Opti-Kappa Analyzer". In this approach, the pulp stream is sampled approximately once every 5 minutes. The pulp sample is screened, washed thoroughly, and diluted significantly. The diluted sample is circulated in a loop where UV light absorption is measured over a prescribed time period and the pulp concentration in the slurry, i.e. pulp consistency, is measured independently. This system involves sampling error, screening error, and pulp consistency measurement error. Although the system provides results much faster than the conventional lab titration process, it is still off-line. The washing requirements of this device are stringent since any small amount of black liquor remaining in the diluted solution will absorb UV light and produce error. Bannier Technology Group (BTG, Inc.) also offers a device which operates on a similar principle but uses UV reflection rather than absorption. The BTG device is marketed under the name "KNA-5000 Kappa Number Analyzer".

All of the investigations and devices discussed so far used broadband lamps as the source of UV light. In 1986, researchers at the National Bureau of Standards (see Horvath, J. J., Semerjian, H. G., "Laser Excited Fluorescence Studies of Black Liquor," *Proceedings of the SPIE*, Vol. 665, June 1986, pp 258– 264) performed fluorescence tests on diluted black liquor samples using a laser as the source of UV light. Although their investigation resulted in better signal to noise ratios, they essentially did not extend the art beyond that of previous investigators. They were only able to obtain a functional relationship between fluorescence and lignin concentration in very dilute samples of black liquor (less than 1300 ppm, which is orders of magnitude less than the in-situ concentrations) and did not investigate pulp at all. They did not provide any insight into how one might be able to use either UV absorption or fluorescence techniques to extend the useful measurement range beyond the highly diluted state.

They did mention that this process was a candidate for in-situ monitoring but provided no rational explanation of how the dilution requirement could be overcome. They did mention that the measurement could be made more acceptable for field use by using optical fibers to guide the UV excitation light to the process stream and carry the fluorescence signal back to the opto-electronics unit.

SUMMARY OF THE INVENTION

Based on a desire to meet the need for an on-line, real-time device which could monitor the concentration of lignin in wood pulp and black liquor, the present invention resulted from a project which examined the fluorescence of black liquor and wood pulp under excitation by various narrowband wavelengths of UV light. It is believed that these wood pulp experiments were the first ever performed and that the results are novel in that a completely unexpected phenomenon was discovered. Namely, when the concentration of lignin in the specimen is increased beyond the very dilute regime, which had been studied earlier by others, the fluorescence signal intensity levels off and then begins to decrease with increasing concentrations of lignin. The region of most interest to on-line pulping is represented by a monotonically decreasing function of fluorescence vs. lignin concentration.

These earlier experiments led to three technical enhancements which improve accuracy and resolution of the measurement of lignin in an undiluted product. These three enhancements are:

1. Use of various single UV wavelengths to discriminate between the fluorescence of lignin and any potential interferents.
2. Use of time resolved fluorescence to eliminate fluorescence from non-lignins and to make the functional relationship between fluorescence and lignin concentration even more steep, thus resulting in improved resolution in highly concentrated substances.
3. Use of phase resolved fluorescence to eliminate the fluorescence from non-lignins.

U.S. Pat. Nos. 5,220,172 and 5,216,483 are based on these ideas.

It is an object of the present invention to provide an on-line measurement of lignin in wood pulp by employing a color shift of fluorescence. Accordingly, one aspect of the present invention is drawn to an apparatus for measuring lignin concentration in at least one undiluted sample on a real-time, in-situ basis. The apparatus comprises light source means for applying excitation light at a selected wavelength to the at least one undiluted sample to produce fluorescent emission light having a spectral distribution of fluorescent intensity. Light detector means are provided for detecting the fluorescent intensity of the emission light and determining the spectral distribution of the fluorescent intensity and establishing signals indicative thereof. Signal processing means are operatively connected to the light detector means for calculating lignin concentration from the spectral distribution signal and producing a signal indicative thereof. Finally, means are provided for displaying the signal indicative of the calculated lignin concentration for viewing by an operator.

Another aspect of the present invention is drawn to a system for controlling a delignification process by measuring lignin concentration in at least one undiluted sample in the process on a real-time, in-situ basis to produce a signal indicative of lignin concentration in the sample. The system comprises light source means for applying excitation light at a selected wavelength to the at least one undiluted sample to produce fluorescent emission light having a spectral distribution of fluorescent intensity. Light detector means are provided for detecting the fluorescent intensity of the emission light and determining the spectral distribution of the fluorescent intensity and establishing signals indicative thereof. Signal processing means are operatively connected to the light detector means for calculating lignin concentration from the spectral distribution signal and producing a signal indicative thereof. Finally, process control elements are provided and connected to the signal processing means for controlling the delignification process in response to the lignin concentration signal.

Yet another aspect of the present invention is drawn to a method for controlling a delignification process by measuring lignin concentration in at least one undiluted sample on a real-time, in-situ basis. The steps of this method comprise: applying an excitation light at a selected wavelength to the at least one undiluted sample to cause the sample to emit fluorescent emission light; determining a spectral distribution of the fluorescent emission light and establishing signals indicative thereof; calculating the lignin concentration in the sample from the spectral distribution signals; and controlling the delignification process by providing the signal indicative of the calculated lignin concentration to process control elements associated with the delignification process and responsive to said lignin concentration signal.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 6 is a schematic block diagram of a system using a band-ratio method according to the present invention.

DESCRIPTION OF THE PREFERRED EMBODIMENTS

When light is absorbed, the absorber is raised to an energy level above the ground state. In most materials, the excess energy is quickly shared via collisions among the molecules in the vicinity of the absorption event resulting in a rise in the temperature. In some cases, however, a portion of the excess energy is given off in the form of a radiated photon. The excitation/emission process is referred to as fluorescence and has been widely used as an analytical technique.

Analytic capability is based on the fact that the spectral distribution of the fluorescent emission, $F(\lambda)d(\lambda)$ (where $\lambda$ is the wavelength) is characteristic of the fluorescing material while the total fluorescence, F, defined by $$F \equiv \int_0^\infty F(\lambda)d\lambda$$

is dependent on the concentration of the fluorescing material.

The approaches described in U.S. Pat. Nos. 5,220,172 and 5,216,483 involve the measurement of the total fluorescence, F. The present invention is based upon using the spectral distribution of the intensity of the fluorescent emission light as a measure of lignin concentration.

Figure 1:
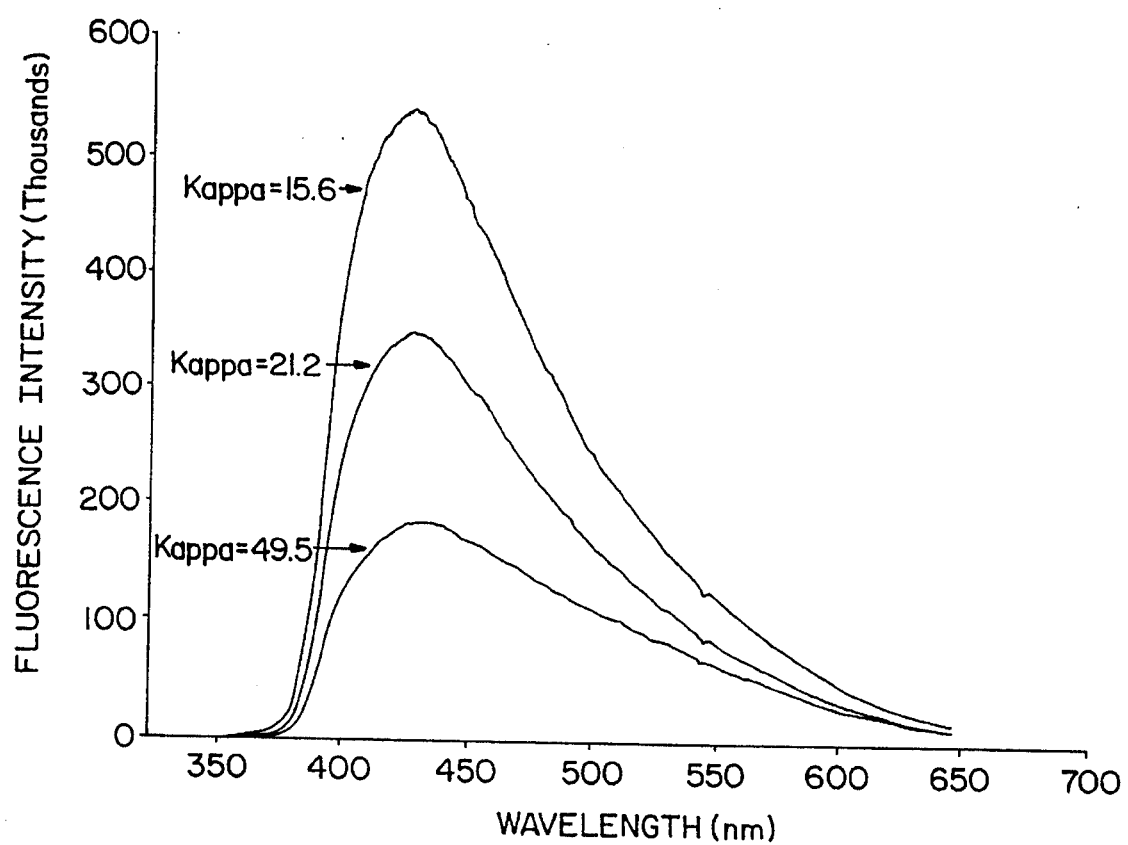
FIG. 1 is a graph plotting fluorescence spectra for pulp samples with three different Kappa numbers.

Fluorescence spectra from all pulp samples in a test series look superficially very much alike, as illustrated in FIG. 1. When normalized to the same height and overlaid for comparison, however, the three curves, derived from three different Kappa numbers, are slightly offset from one another.

In order to quantify this offset shift, the wavelength centroid, $\lambda$ cent, of the spectral emission is calculated by the equation:

$$\lambda \text{ cent} \equiv \frac{\int_0^\infty \lambda F(\lambda)d\lambda}{\int_0^\infty F(\lambda)d\lambda}$$

Figure 2:
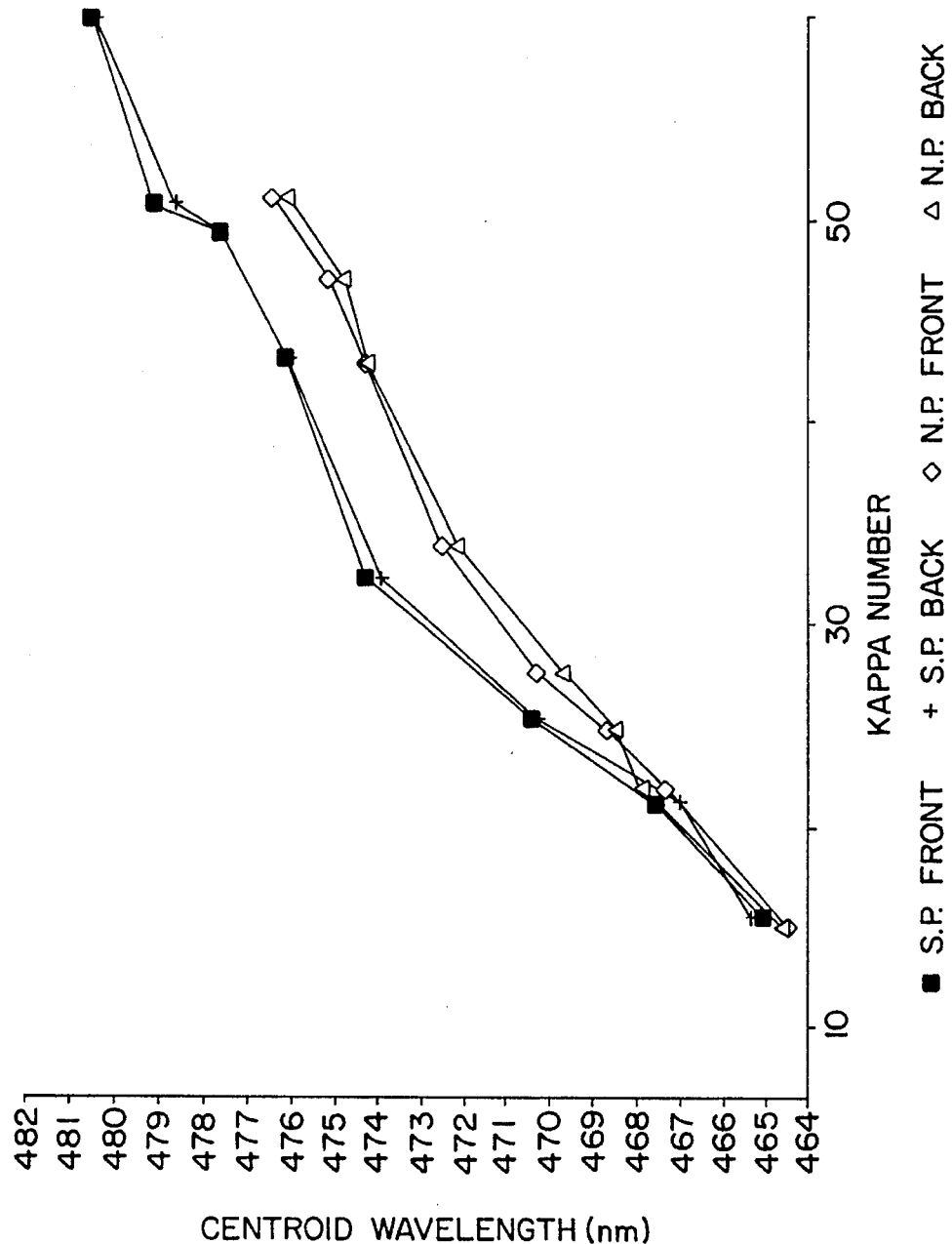
FIG. 2 is a graph plotting wavelength centroid versus Kappa number for pulp samples.

FIG. 2 plots the wavelength centroid, $\lambda$ cent, as a function of the Kappa number of the pulp samples. The Kappa number is the standard measure of the lignin concentration.

As an alternative measure of the spectral shift, the present invention utilizes the ratio, R, of the fluorescence integrated over two wavelength ranges, one comprised of longer wavelengths and the other comprised of shorter wavelengths. Specifically for the data shown in FIG. 3, this is determined by:

$$R \equiv \frac{\int_{\lambda=509}^{\lambda=564} F(\lambda)d\lambda}{\int_{\lambda=371}^{\lambda=427} F(\lambda)d\lambda}$$

where the limits on the integrals are given in nm.

Figure 3:
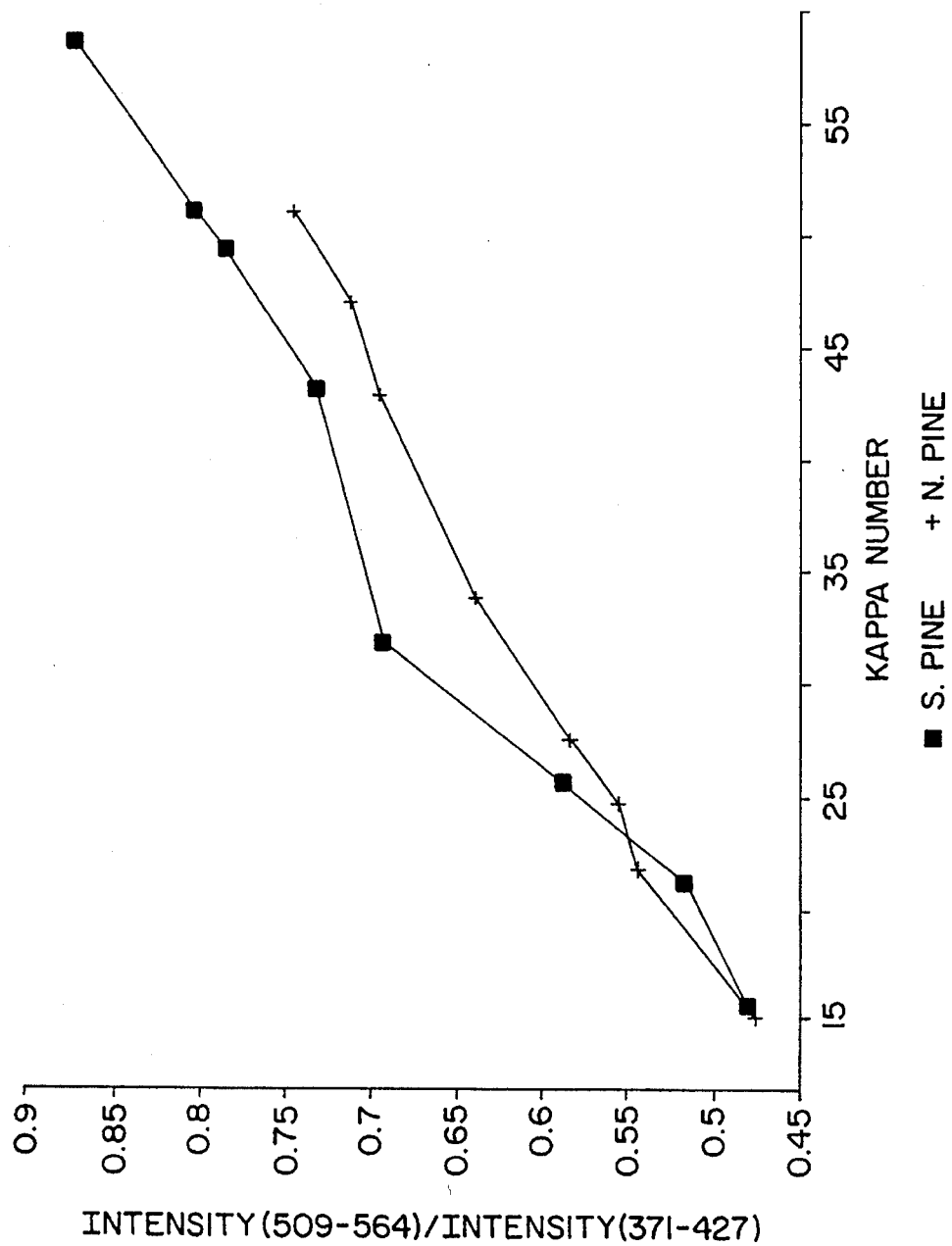
FIG. 3 is a graph plotting a ratio of fluorescence intensity over two emission wavelength ranges versus Kappa numbers.

FIG. 3 shows that this ratio R provides much the same measure of the offset shift as does the wavelength centroid, $\lambda$ cent. Although both approaches provide essentially equivalent results, the hardware required to implement these two approaches is quite different as is described below.

Figure 4:
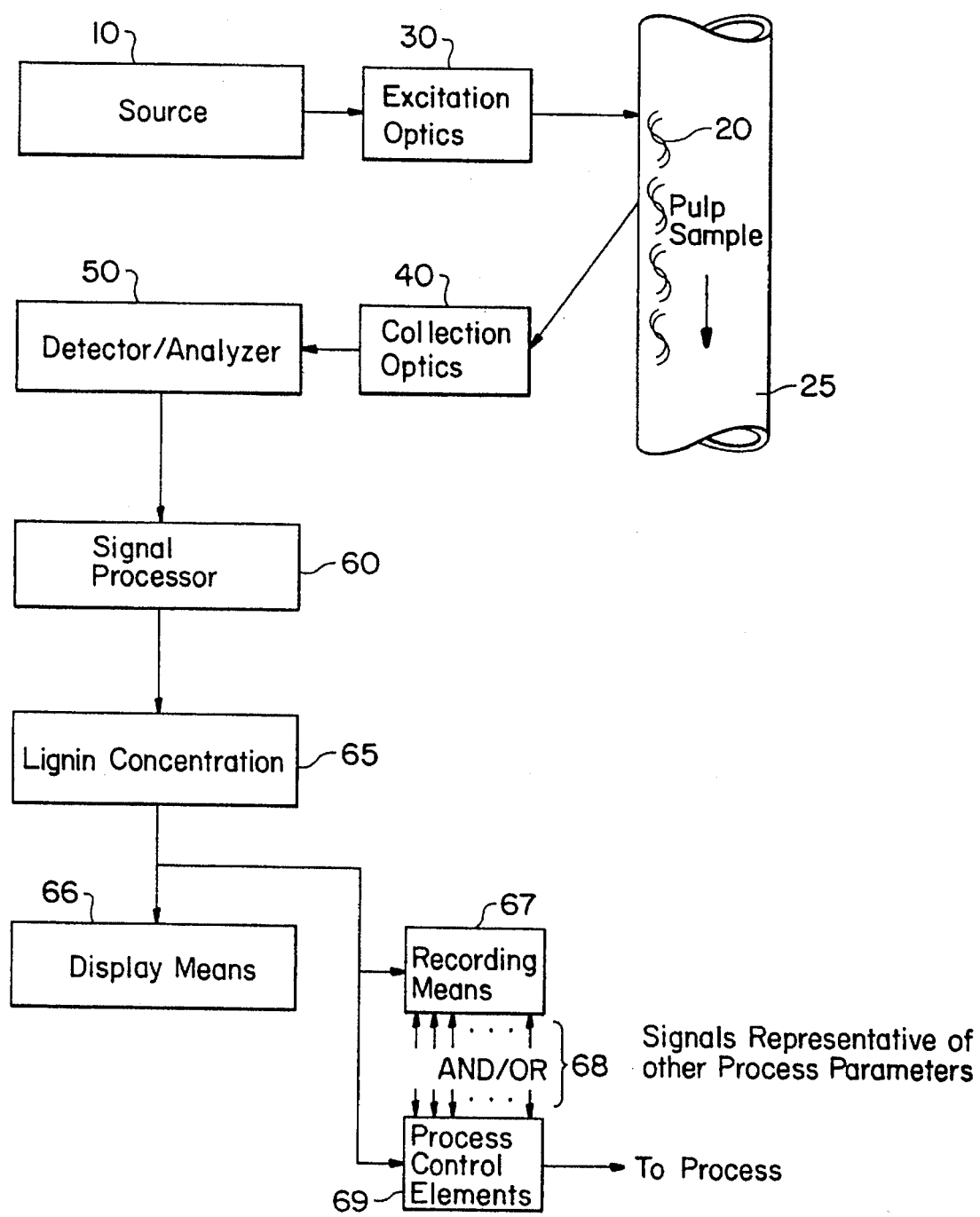
FIG. 4 is a schematic block diagram of a system employing the lignin concentration apparatus according to the present invention.

FIG. 4 is a schematic block diagram of the major components of the present invention. Excitation light from a light source 10 is delivered to an undiluted pulp or liquid sample 20 of interest by excitation optics 30 where it excites the fluorescence of the pulp or liquid sample 20. The pulp or liquid sample 20 is typically being conveyed through a pipe or conduit 25 forming a portion of the overall plant delignification system; alternatively pulp or liquid sample 20 could comprise a bypass line which conveys a portion of the total pulp or liquid flow taken from such a pipe or conduit 25. In either case, a portion of the fluorescent emission light is gathered by the collection optics 40 and delivered to a detector/analyzer 50. A signal processor 60 uses the output from detector/analyzer 50 to produce a calculated lignin concentration signal 65 representative of the calculated lignin concentration in the pulp or liquid sample 20.

The calculated lignin concentration signal 65 can be used in a variety of ways. First, lignin concentration signal 65 can be displayed via display means 66 for viewing by a human operator concerned with the delignification process being monitored. Display means 66 can take any known analog and/or digital form. Second, lignin concentration signal 65 can be sent to one or more process control elements, schematically represented at 69, for use in controlling the pulping/delignification process via known feedforward and/or feedback control elements. These control elements, as known to those skilled in the art, can use other signals 68 representative of other process parameters for the delignification process to control various aspects of the delignification process such as, by way of example and not limitation, the time of cooking of the pulp, the temperature during the process, flow rates of various substances to and from the process, and other controllable factors that affect the composition of the lignin. Indeed, a primary use envisioned for the lignin concentration signal 65 is to provide a continuous, real-time signal for use in feedback control of the paper pulping process and/or for feedforward control of the paper bleaching process. Finally, lignin concentration signal 65 can be sent to recording means, schematically represented at 67 and also of known construction, to produce a time history of the process which, together with signals 68 representative of other process parameters for the delignification process, could be used for later review and analysis. The present invention's ability to produce on-line, in-situ measurements can thus provide new insights into the delignification process and how varying controllable parameters can be used to optimize performance.

A pulsed Nitrogen laser having an output of 337 nm was used as an excitation source for the experimental data shown in FIGS. 2 and 3. This is a convenient, and perhaps preferred source, but the present invention does not require that the source 10 be pulsed, operate at 337 nm, or even be a laser.

In a preferred embodiment, both the excitation optics 30 and the collection optics 40 use optical fibers to allow measurement at points remote from the source 10 and analyzer 50. Again, however, optical fiber based optics are not essential to the operation of the present invention.

The data illustrated in FIGS. 2 and 3 was taken from undiluted pulp samples in conditions simulating those at the last stage of a brownstock washer. This measurement position was chosen for initial consideration because it is where the samples for laboratory analyses are currently taken. There is, however, good reason to consider measurement at other positions in the process as well.

Figure 5:
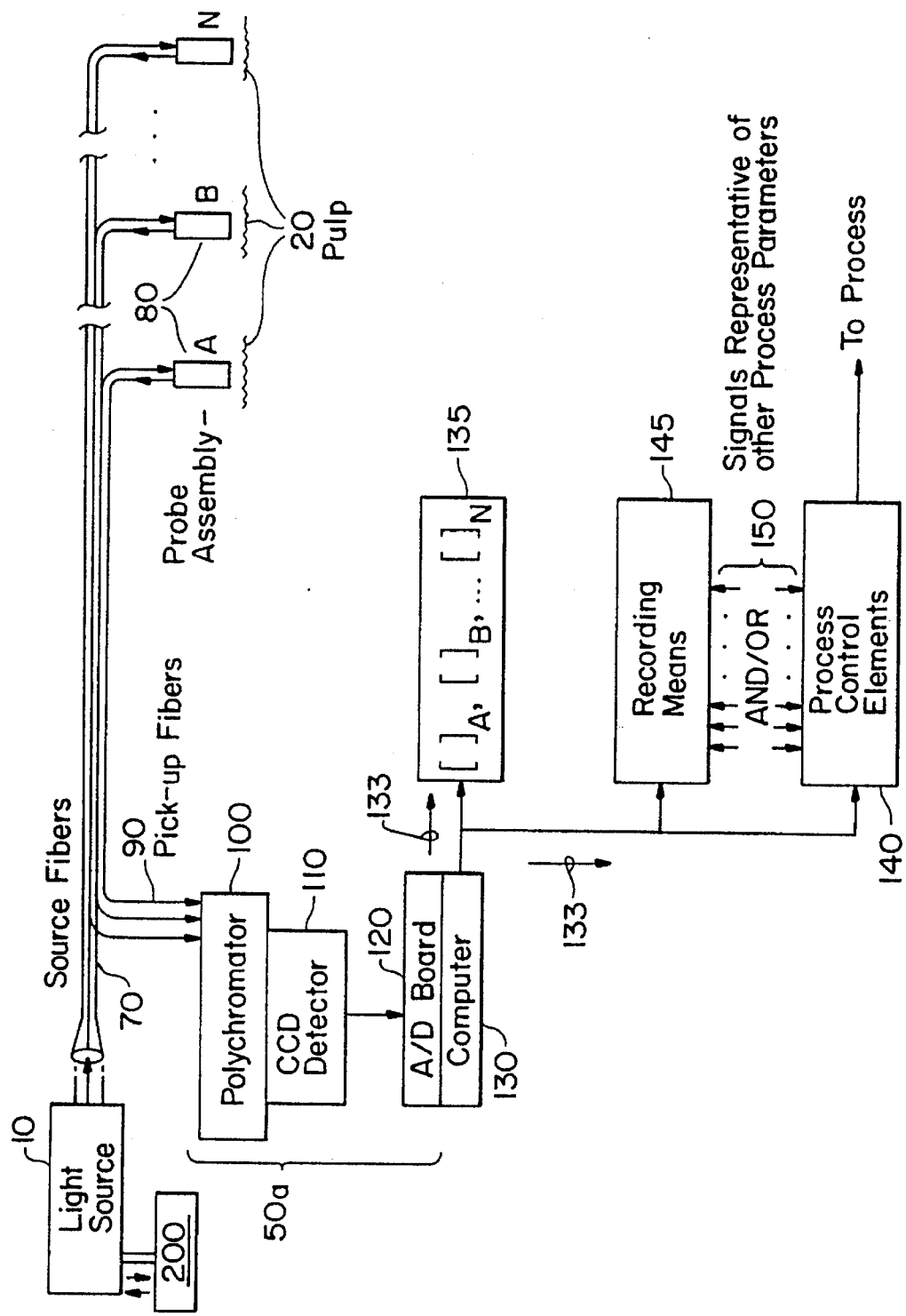
FIG. 5 is schematic block diagram of a system using a wavelength centroid method according to the present invention.

The two methods utilized by the present invention, i.e. (1) the wavelength centroid method and (2) the band-ratio method, utilize different analyzer/detector assemblies. Hardware for the wavelength centroid method is shown in FIG. 5. FIG. 5 shows the system employing fiber optic assemblies 70, 80 and 90 in order to provide measurement at several remote locations A, B . . . N. A single light source 10 provides excitation light along fibers 70 to probe assemblies 80 where it exits the fiber and illuminates the undiluted pulp or liquid sample 20 to be measured. The resultant fluorescent light from the pulp or liquid sample 20 is collected by probe assembly optics 80 and input to return fibers 90 which carry it to an analyzer/detector 50a.

In FIG. 5, the analyzer/detector 50a comprises a polychromator 100 for dispersing the light into a spectrum. Polychromator 100 is operatively connected to a two-dimensional charge-coupled device (CCD) array detector 110 that can simultaneously but separately detect the spectrum from each of the fibers 90. An analog-to-digital A/D converter board 120 is operatively connected to the detector 110 in order to digitize the CCD signals. Signal processing is provided by a computer 130, which is operatively connected to the A/D converter 120, and also controls the detector readout.

The output provided by the computer 130 is the lignin concentration at each of the measurement points A, B . . . . N determined by calculating the wavelength centroid of the light from each probe assembly 80 according to the wavelength centroid method described above. The calculated lignin concentration signal 133 can be displayed on a display 135 for reading by an operator, or the signal can be sent to process control elements schematically represented at 140 for use in controlling the pulping/delignification process via known feedforward and/or feedback control elements. These control elements, as known to those skilled in the art, control various aspects of the delignification process such as, by way of example and not limitation, the time of cooking of the pulp, the temperature during the process, flow rates to and from the process, and other controllable factors that affect the composition of the lignin. Additionally, the calculated lignin concentration signal 133 can be sent to recording means, schematically represented at 145 and of known construction, to produce a time history of the process which, together with signals 150 representative of other process parameters for the delignification process, could be used for later review and analysis.

The hardware used for implementing the band-ratio method according to the present invention is shown in FIG. 6. The light source 10 and fiber optic assemblies and probes 70, 80 and 90 are the same devices used for the wavelength centroid method of FIG. 5. In FIG. 6, an analyzer/detector section 50b comprises a dichroic filter or beam splitter 155 for each measurement point A, B, . . . . N which is operatively connected to pick-up fibers 90 in order to separate the fluorescent light into two desired bands, one comprised of longer wavelengths and the other comprised of shorter wavelengths. A pair of detectors 158 near each dichroic filter or beam splitter 155, for each measurement point, provides a signal proportional to the total fluorescence passed by the dichroic filters or beam splitters 155. Lines 159 provide these signals to a signal processor 160 which comprises circuitry to determine and convert the ratio of the signals from the two wavelength bands to a Kappa number which is output at display means 165, using either analog or digital signal processing techniques. Again, the signal 168 representative of the calculated lignin concentration can be displayed on a display 165 for reading by an operator, or the signal 168 can be sent to process control elements schematically represented at 170 for use in controlling the pulping/delignification process via known feedforward and/or feedback control elements. These control elements, as known to those skilled in the art, again control various aspects of the delignification process such as, by way of example and not limitation, the time of making of the pulp, the temperature during the process, flow rates to and from the process, and other controllable factors that affect the composition of the lignin. Additionally, the calculated lignin concentration signal 168 can again be sent to recording means, schematically represented at 175 and of known construction, to produce a time history of the process which, together with signals 180 representative of other process parameters for the delignification process, could be used for later review and analysis.

For the embodiments shown in FIGS. 4–6, the signal processor 60, the computer 130, and the signal processing electronics 160 would typically measure lignin concentration on a real-time, in-situ basis over a defined time interval. The light sources in each embodiment would apply excitation light at selected wavelengths, for a specified duration, and over the defined time interval. A plurality of signals representative of plural lignin concentration measurements would then be obtained and which could be averaged together to obtain a calculated bulk lignin concentration signal that is representative of the lignin concentration in the bulk material being measured during the defined time interval. Of course, each of these aspects would be selected to suit a given application.

The present invention provides a sensor capable of measuring the lignin concentration in wood pulp at a pulp mill in real-time and in-situ, without the need for sample taking, sample preparation, and sample washing. The systems of the present invention, because they do not require sampling and preparation and because of the "discrimination" enhancements described above, can also be made to be more accurate than other available lignin sensor technologies. Because the systems according to the present invention require no dilution, potential errors due to dilution are eliminated.

The hardware employed by the present invention is easily joined to known fiber optic technology in order to permit hardened probes for single or multiple point sensing of pulp streams. This provides two major advantages. First, the source and analyzer can be located remotely and protected from the harsh environment. Second, a single source/analyzer package can be used via multiplexing to monitor several points in the process stream.

As an alternative to the multiplexing scheme described above, a time share multiplexing scheme could be employed. In this approach, the excitation light would be moved sequentially, such as by drive means schematically represented in FIGS. 5 and 6 at 200, from one delivery fiber to the next, interrogating the various measurement locations in sequence.

The present invention offers additional significant advantages related to the fact that the measurement is based on the relative spectral distribution of the fluorescent light intensity, rather than the absolute magnitude of the fluorescence. Because of this approach, no compensation is required for variations in the excitation source output intensity, variations in the optical efficiency due to alignment changes, fiber transmission loss, etc., or variations due to contamination of the exposed optical surfaces of the probe due to dust, splashes, etc.

The present invention can be applied for excitation by any source that provides measurable fluorescent intensity whether it be a laser or not, and whether it be pulsed or continuous, or by direct illumination or illumination remotely through an optical fiber. The present invention is useful for analysis of dry, undiluted pulp samples or pulp slurries of various consistencies, wood pulp or other process samples that fluoresce, such as petroleum products, food stuffs, pharmaceuticals, etc., and in the application of other methods for quantifying a color shift such as the difference between the intensity of two wavelength bands.

While specific embodiments of the invention have been shown and described in detail to illustrate the application of the principles of the invention, it will be understood that the invention may be embodied otherwise without departing from such principles.

We claim:

1. An apparatus employing a color shift of fluorescence for measuring lignin concentration in at least one undiluted sample on a real-time, in-situ basis based upon a spectral distribution of fluorescent emission light from the sample, comprising:

light source means for applying excitation light at a selected wavelength to the at least one undiluted sample for causing the sample to produce fluorescent emission light having a spectral distribution of fluorescent intensity;

light detector means for detecting the fluorescent intensity of the emission light and determining the spectral distribution of fluorescent intensity and establishing signals indicative thereof;

signal processing means operatively connected to the light detector means for calculating a lignin concentration from the spectral distribution signals and producing a signal indicative thereof; and means for displaying the signal indicative of the calculated lignin concentration for viewing by an operator.

2. The apparatus according to claim 1, comprising probe means, connected to the light source means and the light detector means, located at the at least one sample for conveying the excitation light to the at least one sample and conveying the fluorescent emission light to the light detector means.

3. The apparatus according to claim 1, wherein the light detector means comprises polychromator means for dispersing the fluorescent intensity of the emission light into a spectrum.

4. The apparatus according to claim 3, wherein the light detector means further comprises array detector means operatively connected to the polychromator means for simultaneously and separately detecting the spectrum of a plurality of samples.

5. The apparatus according to claim 4, wherein the light detector means further comprises analog-to-digital converter means operatively connected to the array detector means for converting the spectral distribution signals into a digital signal.

6. The apparatus according to claim 4, wherein the array detector means comprises a two-dimensional charge-coupled device (CCD) array detector.

7. The apparatus according to claim 5, wherein the signal processing means comprises control means for controlling the polychromator means and the array detector means and for outputting the digital signal.

8. The apparatus according to claim 7, comprising a plurality of samples.

9. The apparatus according to claim 8, comprising probe means connected to the light source means and the polychromator means and located at the samples for conveying the excitation light to the samples and for conveying the fluorescent emission light of the samples to the polychromator means.

10. The apparatus according to claim 1, wherein the light detector means comprises filter means for separating the fluorescent intensity of the emission light into two bands.

11. The apparatus according to claim 10, wherein the light detector means further comprises detecting means for detecting each band and conveying a signal proportional to the fluorescent intensity of each band of the emission light.

12. The apparatus according to claim 11, wherein the signal processing means converts the proportional signals into a Kappa number.

13. The apparatus according to claim 12, comprising a plurality of samples.

14. The apparatus according to claim 13, comprising probe means connected to the light source means and the filter means and located at the samples for conveying the excitation light to the samples and for conveying the fluorescent emission light from the samples to the filter means.

15. The apparatus according to claim 1, wherein the light source means is a laser.

16. The apparatus according to claim 1, wherein the light source means is a pulsed laser.

17. The apparatus according to claim 16, wherein the light source means is a pulsed nitrogen laser.

18. The apparatus according to claim 17, wherein the light source means is a pulsed nitrogen laser having an output of 337 nm.

19. The apparatus according to claim 1, comprising:

means for calculating the lignin concentration from the spectral distribution signals a plurality of times over a defined time interval to produce a plurality of lignin concentration signals; and means for processing said plurality of lignin concentration signals to produce a calculated bulk lignin concentration signal that is representative of the lignin concentration in the sample during the defined time interval.

20. A system for controlling a delignification process which employs a color shift of fluorescence to measure lignin concentration in at least one undiluted lignin sample in the process on a real-time, in-situ basis to produce a signal indicative of lignin concentration in the sample based upon a spectral distribution of fluorescent emission light from the sample, comprising:

light source means for applying excitation light at a selected wavelength to the at least one undiluted sample for causing the sample to produce fluorescent emission light having a spectral distribution of fluorescent intensity;

light detector means for detecting the fluorescent intensity of the emission light and determining the spectral distribution of fluorescent intensity and establishing signals indicative thereof;

signal processing means operatively connected to the light detector means for calculating lignin concentration from the spectral distribution signals and producing a signal indicative thereof; and process control elements, connected to the signal processing means, for controlling the delignification process in response to the lignin concentration signal.

21. The system according to claim 20, comprising recording means for recording the variation with time of said lignin concentration signal and other process parameters associated with the delignification process, to produce a time history of these process parameters.

22. A method for controlling a delignification process which employs a color shift of fluorescence to measure lignin concentration in at least one undiluted sample in the process on a real-time, in-situ basis to produce a signal indicative of lignin concentration in the sample based upon a spectral distribution of fluorescent emission light from the sample, the method comprising the steps of:

applying an excitation light at a selected wavelength to the at least one undiluted sample to cause the sample to emit fluorescent emission light;

determining a spectral distribution of the fluorescent emission light and establishing signals indicative thereof;

calculating the lignin concentration from the spectral distribution signals; and controlling the delignification process by providing the signal indicative of the calculated lignin concentration to process control elements associated with the delignification process and responsive to said lignin concentration signal.

23. The method according to claim 22, further comprising the steps of:

calculating the lignin concentration from the spectral distribution signals a plurality of times over a defined time interval to produce a plurality of lignin concentration signals; and processing said plurality of lignin concentration signals to produce a calculated bulk lignin concentration signal that is representative of the lignin concentration in the sample during the defined time interval.

* * * * *